(12) United States Patent
Bussmann et al.

(10) Patent No.: US 11,518,749 B2
(45) Date of Patent: Dec. 6, 2022

(54) METHOD FOR THE CONTINUOUS SEPARATION BY DISTILLATION OF MIXTURES THAT CONTAIN MORPHOLINE (MO), MONOAMINODIGLYCOL (ADG), AMMONIA, WATER AND METHOXYETHANOL (MOE)

(71) Applicant: BASF SE, Ludwigshafen am Rhein (DE)

(72) Inventors: Oliver Bussmann, Ludwigshafen am Rhein (DE); Eva Koch, Ludwigshafen am Rhein (DE); Manfred Heilig, Ludwigshafen am Rhein (DE); Joachim Pfeffinger, Ludwigshafen am Rhein (DE); Joerg Pastre, Ludwigshafen am Rhein (DE); Johann-Peter Melder, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 108 days.

(21) Appl. No.: 16/971,650

(22) PCT Filed: Feb. 11, 2019

(86) PCT No.: PCT/EP2019/053273
§ 371 (c)(1),
(2) Date: Aug. 20, 2020

(87) PCT Pub. No.: WO2019/162121
PCT Pub. Date: Aug. 29, 2019

(65) Prior Publication Data
US 2020/0392093 A1 Dec. 17, 2020

(30) Foreign Application Priority Data

Feb. 22, 2018 (EP) .................................... 18158097
Feb. 27, 2018 (EP) .................................... 18158951

(51) Int. Cl.
| | | |
|---|---|---|
| C07C 217/08 | (2006.01) |
| C07C 41/42 | (2006.01) |
| C07C 213/02 | (2006.01) |
| C07C 213/10 | (2006.01) |
| C07D 295/03 | (2006.01) |
| C07D 295/023 | (2006.01) |

(52) U.S. Cl.
CPC .......... C07D 295/023 (2013.01); C07C 41/42 (2013.01)

(58) Field of Classification Search
CPC ..... C07C 217/08; C07C 41/42; C07C 213/02; C07C 213/10; C07D 295/03
See application file for complete search history.

(56) References Cited

U.S. PATENT DOCUMENTS

| | | | |
|---|---|---|---|
| 3,154,544 A | 10/1964 | Langdon et al. | |
| 3,155,657 A | 11/1964 | Bedoit, Jr. | |
| 4,256,880 A | 3/1981 | Frech et al. | |
| 4,739,051 A | 4/1988 | Schroeder et al. | |
| 7,825,281 B2 | 11/2010 | Schmidtke et al. | |
| 8,197,646 B2 * | 6/2012 | Schmidtke ......... | C07D 295/027 203/99 |
| 8,246,793 B2 | 8/2012 | Schmidtke et al. | |
| 8,293,075 B2 | 10/2012 | Schmidtke et al. | |
| 8,487,135 B2 | 7/2013 | Kubanek et al. | |
| 2008/0255351 A1 | 10/2008 | Hoffer et al. | |

FOREIGN PATENT DOCUMENTS

| | | |
|---|---|---|
| CN | 102002019 A | 4/2011 |
| CN | 102206196 A | 10/2011 |
| CN | 104262173 A | 1/2015 |
| CN | 104262177 A | 1/2015 |
| DE | 1049864 B | 2/1959 |
| DE | 3002342 A1 | 2/1981 |
| DE | 3125662 A1 | 1/1983 |
| DE | 102005047458 A1 | 4/2007 |
| EP | 70397 A1 | 1/1983 |
| EP | 167872 A3 | 12/1986 |
| EP | 514692 A3 | 3/1993 |
| EP | 696572 A1 | 2/1996 |
| WO | 2007/036496 A1 | 4/2007 |

(Continued)

OTHER PUBLICATIONS

European Search Report for EP Patent Application No. 18158097.8, dated Jul. 25, 2018, 3 pages.
International Preliminary Report on Patentability received for PCT Patent Application No. PCT/EP2019/053273, dated Sep. 3, 2020, 12 pages. (5 pages of English Translation and 7 pages of Original Document).
International Search Report and Written Opinion received for PCT Patent Application No. PCT/EP2019/053273, dated Apr. 24, 2019, 14 pages. (6 pages of English Translation and 8 pages of Original Document).
Roose, et al., "Amines, Aliphatic : 6—Cyclic Amines", Ullmann's Encyclopedia of Industrial Chemistry, Sep. 30, 2015, pp. 21-27.
International Search Report for PCT/EP2019/053269 dated May 2, 2019.

(Continued)

Primary Examiner — Sun Jae Yoo
(74) Attorney, Agent, or Firm — Faegre Drinker Biddle & Reath LLP

(57) ABSTRACT

A process for the continuous distillative separation of mixtures comprising morpholine (MO), monoaminodiglycol (ADG), ammonia, water and methoxyethanol (MOE), obtained by reacting diethylene glycol (DEG) with ammonia, wherein ammonia, water, ADG and DEG are removed by distillation and the resulting stream comprising MO and MOE is supplied to a distillation column K40 in which at a top pressure of from 20 to 2000 mbar MO, MOE and organic products having a boiling point 128° C. (1.013 bar) are removed via the bottom and organic products having a boiling point 128° C. are removed overhead, and also MO is removed via a side draw, where K40 is equipped with an evaporator for heating the bottoms, into which is fed heating vapor having a pressure of from 1 to 10 bar.

20 Claims, 5 Drawing Sheets

(56) References Cited

FOREIGN PATENT DOCUMENTS

Figure 1:
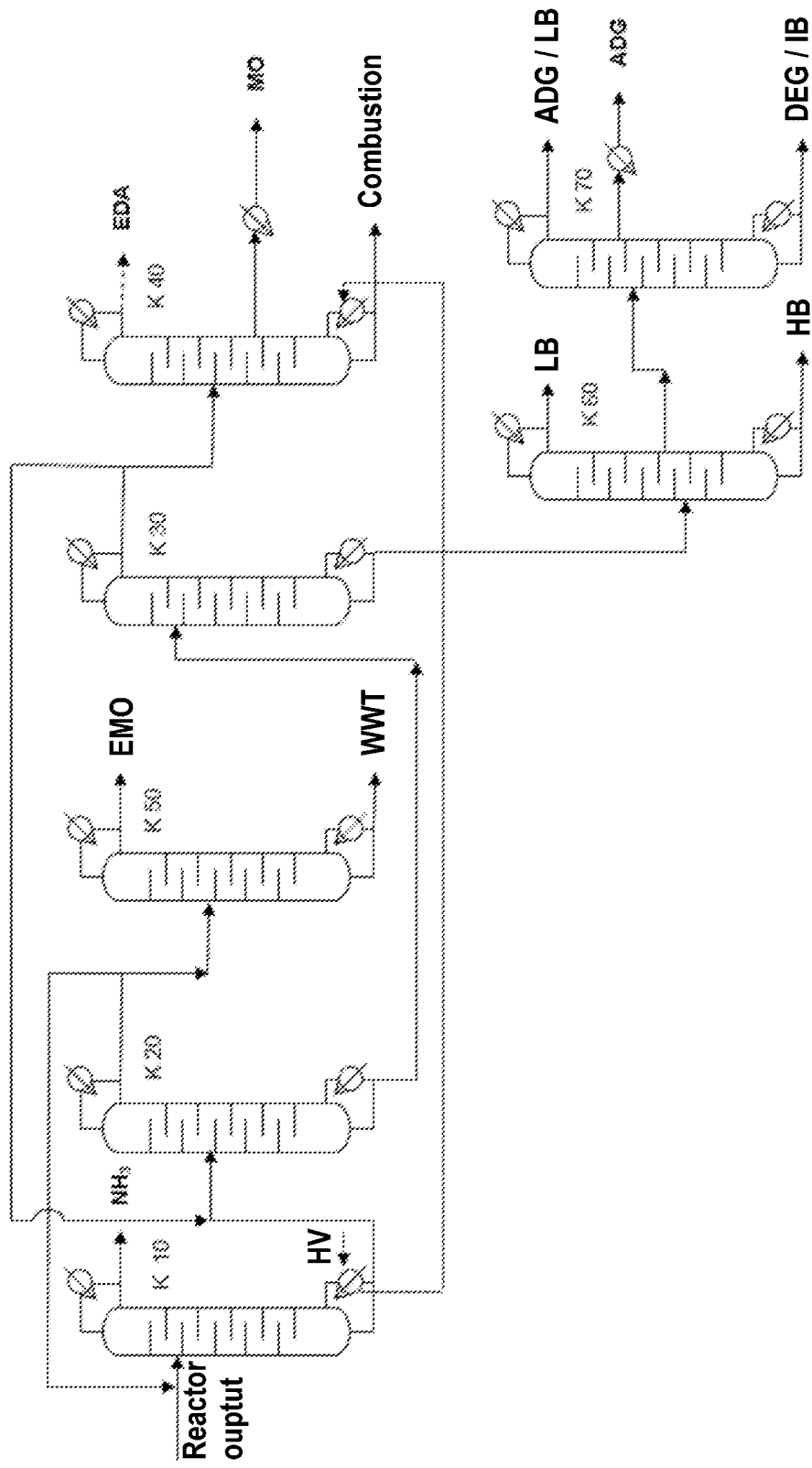

| WO | WO-2008037587 A1 | 4/2008 |
| WO | WO-2008037589 A1 | 4/2008 |
| WO | WO-2008037590 A1 | 4/2008 |
| WO | WO-2008037659 A1 | 4/2008 |
| WO | WO-2011067199 A1 | 6/2011 |

OTHER PUBLICATIONS

International Search Report for PCT/EP2019/053273 dated Apr. 24, 2019.
Written Opinion of the International Searching Authority for PCT/EP2019/053269 dated May 2, 2019.
Written Opinion of the International Searching Authority for PCT/EP2019/053273 dated Apr. 24, 2019.

* cited by examiner

METHOD FOR THE CONTINUOUS SEPARATION BY DISTILLATION OF MIXTURES THAT CONTAIN MORPHOLINE (MO), MONOAMINODIGLYCOL (ADG), AMMONIA, WATER AND METHOXYETHANOL (MOE)

CROSS-REFERENCE TO RELATED APPLICATIONS

This application is a national stage application (under 35 U.S.C. § 371) of PCT/EP2019/053273, filed Feb. 11, 2019, which claims benefit of European Application Nos. 18158097.8, filed Feb. 22, 2018, and 18158951.6, filed Feb. 27, 2018, all of which are incorporated herein by reference in their entirety.

The present invention relates to a process for the continuous distillative separation of mixtures comprising morpholine (MO), monoaminodiglycol (ADG), ammonia, water and methoxyethanol [=2-methoxyethanol=methyl glycol] (MOE), obtained by reacting diethylene glycol (DEG) of the formula

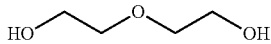

with ammonia.

Aminodiglycol (ADG) [=2-(2-aminoethoxy)ethanol=2,2'-aminoethoxyethanol, formula

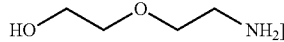

and morpholine are used, inter alia, as solvents, stabilizers, for the synthesis of chelating agents, synthetic resins, medicaments, inhibitors and interface-active substances.

N-Ethylmorpholine (EMO) is used, inter alia, as a catalyst for the preparation of polyurethane foams.

Numerous processes are described in the literature for the preparation of ADG and morpholine.

Ullmann's Encyclopedia of Industrial Chemistry, 6th Edition, 2000 electronic release, Wiley-VCH Verlag, heading 'Cyclic amines' in the chapter 'Aliphatic amines' describes the synthesis of ADG and MO by amination of DEG under hydrogen pressure and in the presence of a cobalt or nickel catalyst (citations: EP-A-696 572 (BASF AG), DE-A-1 049 864) or other catalysts (citations: DE-A-3 002 342, DE-A-3 125 662 (BASF AG), U.S. Pat. No. 3,155,657).

The earlier German patent application No. 102005047458.6 of Sep. 30, 2005 and the earlier European follow-on patent application No. 06101339.7 of Feb. 6, 2006 (BASF AG) relate to a process for the preparation of ADG and morpholine by reacting DEG with ammonia in the presence of a specific copper, nickel and cobalt heterogeneous catalyst and also the workup by multistage distillation in general.

The two patent applications WO 2008/037589 A1 and WO 2008/037590 A1 (both BASF AG) relate to processes for the continuous distillative separation of mixtures comprising morpholine (MO), monoaminodiglycol (ADG), ammonia and water, obtained by reacting diethylene glycol (DEG) with ammonia.

WO 2008/037587 A1 (BASF AG) also relates to a process for the continuous distillative separation of mixtures comprising morpholine (MO), monoaminodiglycol (ADG), ammonia and water, obtained by reacting diethylene glycol (DEG) with ammonia. Specifically, the distillation of crude morpholine at a pressure of 2.2 $bar_{abs}$ is disclosed.

WO 2008/037659 A1 relates to a process for preparing electronics-grade ADG.

CN 102002019 A describes a distillative method for removing methoxyethanol from morpholine. For this, water vapor is fed into the relevant distillation column. This exploits the fact that methoxyethanol forms an azeotrope with water.

CN 104262173 A and CN 104262177 A both describe a process for reacting DEG with ammonia. CN 104262177 A further describes a process for working up the resulting mixture.

The synthesis of morpholine and monoaminodiglycol is characterized by the formation of a large number of secondary components. The removal of the unconverted feedstocks, products of value and by-products is effected by distillation, which leads to considerable expenditure in terms of apparatus and energy.

On account of the fact that their boiling points lie close together, the separation of morpholine and methoxyethanol is difficult in particular. This is compounded by the fact that the requirements for the purity of morpholine have risen continuously in recent years.

It was an object of the present invention, while overcoming a disadvantage or a plurality of disadvantages of the prior art, to find an improved, economical, especially energy-efficient, process for the separation of mixtures comprising morpholine (MO), monoaminodiglycol (ADG), ammonia, water and methoxyethanol and optionally N-ethylmorpholine (EMO) and optionally 1,2-ethylenediamine (EDA) and optionally organic products having a boiling point >224.8° C. (1.013 bar). The individual organic components (amines), in particular MO and ADG and optionally EMO, should be obtained here in high purity and quality (e.g. color quality).

Accordingly, a process was found for the continuous distillative separation of mixtures comprising morpholine (MO), monoaminodiglycol (ADG), ammonia, water and methoxyethanol (MOE), obtained by reacting diethylene glycol (DEG) with ammonia, which is characterized in that ammonia, water, ADG and DEG are removed by distillation and the resulting stream comprising MO and MOE is supplied to a distillation column 40 in which at a top pressure of from 20 to 2000 mbar MO, MOE and organic products having a boiling point ≥128° C. (1.013 bar) are removed via the bottom and organic products having a boiling point >128° C. are removed overhead, and also MO is removed via a side draw, where K40 is equipped with an evaporator for heating the bottoms, into which is fed heating vapor having a pressure of from 1 to 10 bar. Surprisingly, it has been found that a markedly improved removal of MOE is possible in the pressure range according to the invention. It is assumed that under the distillation conditions according to the invention MOE and MO form a low-boiling azeotrope which can be withdrawn via the sump. It is therefore possible, for example, to dispense with the additional feeding in of water vapor into K40 in order to remove MOE as a water/MOE azeotrope.

Furthermore, it has been found that K40 can be operated with heating vapor which has only a low pressure of from 1 to 10 bar. This pressure is preferably 1 to 8 bar, particularly preferably 1 to 6 bar and very particularly preferably 2 to 5 bar or even 2 to 3 bar. In addition, it has been found that such heating vapor as described hereinbelow can be obtained by means of flash evaporation of a condensate resulting from the condensation of heating vapor in a heat exchanger, wherein the heating vapor prior to its condensation in the heat exchanger has a pressure of from 2 to 50 bar (see hereinbelow).

Unless otherwise indicated, figures for pressure in the respective distillation columns and evaporators and also of the heating vapor relate to absolute pressure.

Unless otherwise indicated, the following figures relating to the pressure in the respective distillation columns relate to the top pressure.

The reaction of DEG with ammonia is typically effected in a reactor C1, wherein DEG and ammonia are heated prior to entry into C1 by means of a heat exchanger W2 into which is fed heating vapor having a pressure of from 2 to 50 bar, preferably 3 to 45 bar, particularly preferably 4 to 40 bar.

The reaction of DEG and ammonia is typically effected in the presence of hydrogen and a heterogeneous hydrogenation catalyst (also referred to as catalyst hereinbelow). In this case, the hydrogen is preferably recycled into the reactor as cycle gas via a high-pressure separator.

In the reaction of DEG and ammonia, the embodiments (A) and (B) are preferred in particular. Hereinbelow, embodiment (A) is firstly described and then embodiment (B).

In the preferred embodiment (A), the conversion based on DEG is preferably 40% to 90% (for example 40% to 75%), preferably 50% to 80%, particularly preferably 50% to 75%, or even 50% to 70%.

The reaction of diethylene glycol (DEG) with ammonia is preferably effected in the presence of hydrogen and a heterogeneous hydrogenation catalyst, wherein
the conversion based on DEG is 40% to 90% (for example 40% to 75%), preferably 50% to 80%, particularly preferably 50% to 75%, or even 50% to 70%,
the reaction is effected at a pressure of from 100 to 300 bar and a temperature of from 170° C. to 220° C.,
the molar ratio of ammonia to DEG is 4 to 10, and
the catalyst hourly space velocity is in the range from 0.05 to 5 kg, preferably 0.1 to 2 kg, of diethylene glycol (DEG) per liter of catalyst (bed volume) and per hour.

The heterogeneous hydrogenation catalyst mentioned in the preceding paragraph preferably comprises Cu, Ni and aluminum oxide as support. In a particularly preferred heterogeneous hydrogenation catalyst, the catalytically active composition of the catalyst prior to treatment with hydrogen comprises oxygen-containing compounds of aluminum, copper, nickel and cobalt and in the range from 0.2% to 5.0% by weight of oxygen-containing compounds of tin, calculated as SnO. Catalysts of this type are described, for example, in WO 2011/067199 A1 (BASF SE). In particular, catalysts are used, the catalytically active composition of which, prior to the reduction thereof with hydrogen, comprises in the range from
15% to 80% by weight of oxygen-containing compounds of aluminum, calculated as $Al_2O_3$,
1% to 20% by weight of oxygen-containing compounds of copper, calculated as CuO,
5% to 35% by weight of oxygen-containing compounds of nickel, calculated as NiO,
5% to 35% by weight of oxygen-containing compounds of cobalt, calculated as CoO, and
0.2% to 5.0% by weight of oxygen-containing compounds of tin, calculated as SnO.

The mixture used in the process according to the invention is particularly preferably prepared according to WO 2011/067199 A1 (BASF SE).

At a conversion of at most 75%, embodiment (A) corresponds to an ADG-oriented mode of operation. That is to say, correspondingly more ADG than morpholine (MO) is formed.

In the other preferred embodiment (B), catalyst, comprising Cu and Ni on aluminum oxide as support, as described in particular in EP-A-70 397 (BASF AG), is used. Catalysts of this type are also described in EP-A-514 692 and EP-A-167 872 (both BASF AG).

In a catalyst which is particularly preferred here, the catalytically active composition of the catalyst prior to treatment with hydrogen comprises in the range from 25% to 65% by weight of aluminum oxide ($Al_2O_3$), 30% to 60% by weight of oxygen-containing compounds of copper, calculated as CuO, and 5% to 15% by weight of oxygen-containing compounds of nickel, calculated as NiO.

The reactor temperature preferred for the reaction of diethylene glycol (DEG) with ammonia is in the range from 190-235° C. here. An isothermal reactor operation mode is preferred. The pressure preferred for the reaction of diethylene glycol (DEG) with ammonia is in the range from 20 to 30 bar.

The molar ratio of ammonia to DEG is preferably in the range from 1:1 to 50:1.

The DEG conversion is preferably in the range from 80% to 98%.

The catalyst hourly space velocity is generally in the range from 0.01 to 2, preferably 0.05 to 0.5 kg, of diethylene glycol (DEG) per liter of catalyst (bed volume) and per hour.

Embodiment (B) corresponds to an MO-oriented mode of operation. That is to say, correspondingly more morpholine (MO) than ADG is formed.

The reaction of embodiment (A) is preferred over the reaction of embodiment (B).

Preferably, for the distillative removal of ammonia, water, ADG and DEG, the ammonia is removed overhead in a first distillation column K10, the bottoms output from K10 is supplied to a second distillation column K20, in which water and organic products are removed overhead at a top temperature of from 45 to 198° C. and a top pressure of from 0.1 to 15 bar, and the bottoms output from K20 is supplied to a third distillation column K30, in which MO, MOE and organic products having a boiling point <140° C. (1.013 bar) (stream comprising MO and MOE) are removed overhead or via a side draw and ADG, DEG and organic products having a boiling point of >190° C. (1.013 bar) are removed via the bottom.

The organic products removed in column K40 via the bottom are typically disposed of, for example combusted, because of the high content of methoxyethanol (MOE).

Column K10 preferably has in the range from 3 to 30, in particular in the range from 5 to 20, theoretical plates.

It is preferably operated at a pressure in the range from 5 to 30 bar, in particular 10 to 20 bar.

The feed point for column K10 is preferably located in the upper third, based on the number of theoretical plates.

Column K20 preferably has in the range from 25 to 70, in particular in the range from 30 to 60, theoretical plates.

It is preferably operated at a pressure in the range from 0.1 to 10 bar, in particular 0.8 to 7 bar.

The feed point for column K20 is preferably located in the middle third, based on the number of theoretical plates.

Water is preferably removed in column K20. Organic products, which in some cases have higher boiling points than the bottoms product morpholine, are preferably removed overhead with this water as a minimum azeotrope.

In an ADG-oriented mode of operation (see above), there is the problem that many high boilers (especially ADG and DEG) are present in the bottoms of the columns K10 and K20, resulting in correspondingly high bottom temperatures. This poses a problem in particular for already existing installations which were originally designed with an MO-oriented mode of operation in mind. This is to be understood to mean a mode of operation in which a correspondingly large amount of morpholine is produced compared to ADG. Here, the amount of the high-boiling components DEG and ADG is consequently much lower than in an ADG-oriented mode of operation.

If such installations are now to be operated in an ADG-oriented manner, on account of the relatively high content of the high-boiling components DEG and ADG the problem may arise that the heating vapor conventionally available (for such installations), which typically has a pressure of up to 50 bar, is no longer sufficient for adequately supplying heat to the bottom of K10 and K20. In addition, there is the problem of reduced product quality, caused by the high bottom temperatures. This is compounded by the disadvantage that heating vapor having an appropriately high pressure (for example above 50 bar) is producible only with great expense, especially with respect to the energy required to do so.

Therefore, the stream comprising water and organic products which is removed overhead at column K20 is preferably partially recycled into the feed or bottom of column K10. Preferably, 10% to 80% by weight, particularly preferably 20% to 70% by weight, is recycled.

Likewise preferably, the stream comprising MO and MOE which is removed overhead at column K30 and/or the stream obtained at the side draw from K40 (morpholine) is/are partially recycled into the feed of column K20. Preferably, overall, 20% to 90% by weight, particularly preferably 25% to 80% by weight, of the streams obtained from K30 and/or K40 are recycled. In the case of recycling from both columns, the percentages of the preceding sentence are based on the sum total of the streams obtained from K30 overhead and K40 at the side draw. Such a recycling from K30 and/or K40 is especially advantageous when the pressure in column K20 is in the range from 1.5 to 10 bar, or 2 to 7 bar.

The bottom temperature in K10 and K20 can be reduced by means of the respective recycling. In this way the product quality can be improved and said distillation columns can be operated with conventionally available heating vapor. The heating vapor fed into the evaporators of K10 and K20 therefore in particular has a pressure in accordance with the (preferred) ranges specified below for these columns.

Column K30 preferably has in the range from 5 to 25, in particular in the range from 7 to 20, theoretical plates.

It is preferably operated at a pressure in the range from 0.01 to 5 bar, in particular 0.1 to 2.5 bar.

The feed point for column K30 is preferably located in the upper third, based on the number of theoretical plates.

In the alternative embodiment, the side draw is preferably located 1 to 8 theoretical plates, in particular 2 to 6 theoretical plates, above the feed point.

Column K40 preferably has in the range from 10 to 80, in particular in the range from 15 to 60, theoretical plates.

It is preferably operated at a pressure in the range from 30 to 1500 mbar, particularly preferably 50 to 800 mbar and very particularly preferably 80 to 750 mbar, for example 100 to 500 mbar or even 100 to 450 mbar.

The feed point for column K40 is preferably located in the upper or middle, in particular middle, third, based on the number of theoretical plates.

The MO side draw lying opposite is preferably located 1 to 30 theoretical plates, in particular 2 to 25 theoretical plates, below the feed point.

In column K40, organic products having a boiling point ≤128° C. (1.013 bar), preferably <128° C. (1.013 bar), such as for example EDA, are removed overhead and organic products having a boiling point ≥128° C. (1.013 bar) are removed via the bottom.

The organic products removed overhead in column K40, especially EDA, may advantageously be wholly or partially recycled into the feed to column K20.

In a further embodiment, further distillative purification of the top distillate can afford pure EDA as product of value.

In one particular embodiment, the stream comprising water and organic products which is removed overhead at column K20 is supplied to a column K50 in which aqueous N-ethylmorpholine solution (aqueous EMO solution) is removed overhead or via a liquid side draw, wherein the liquid side draw is preferably located in the upper third of the column based on the number of theoretical plates, and water is removed via the bottom.

Column K50 preferably has in the range from 10 to 50, in particular in the range from 15 to 40, theoretical plates.

It is preferably operated at a pressure in the range from 0.1 to 16 bar, in particular 0.2 to 8 bar.

The feed point for column K50 is preferably located in the upper or middle third, in particular in the middle third, based on the number of theoretical plates.

The aqueous N-ethylmorpholine solution is first dewatered to obtain pure EMO. The dewatering agent used is preferably sodium hydroxide solution, for example as 40%-60% by weight aqueous solution, in particular 50% by weight aqueous solution. The dewatering with the sodium hydroxide solution is preferably conducted continuously in an extraction column. The extraction temperature is preferably between 25-60° C., in particular between 30-55° C. The sodium hydroxide solution is diluted in the process to 15%-35% by weight, in particular 20%-30% by weight.

After the phase separation, the organic phase is worked up in a continuous or batch distillation. The distillation is preferably conducted batchwise in a distillation still.

The top products are obtained in this case in succession: optionally ethylamine, optionally ethanol as aqueous azeotrope, optionally N-methylmorpholine as an aqueous azeotrope, optionally anhydrous N-methylmorpholine and the product of value N-ethylmorpholine (EMO).

In a preferred embodiment, the bottoms output from K30 is supplied to a distillation column K60 in which ADG is removed in a side draw, organic products having a boiling point ≤224.8° C. (1.013 bar) are removed overhead and organic products having a boiling point >255° C. (1.013 bar) are removed via the bottom.

Column K60 preferably has in the range from 20 to 80, in particular in the range from 30 to 70, theoretical plates.

It is preferably operated at a pressure in the range from 0.005 to 1 bar, in particular 0.01 to 0.7 bar.

The feed point for column K60 is preferably located in the middle or lower, in particular middle, third, based on the number of theoretical plates.

The ADG side draw lying opposite is preferably located 1 to 30, in particular 2 to 20, theoretical plates above the feed point.

In a preferred embodiment, the organic products removed overhead in column K60, such as for example N-(2-aminoethyl)morpholine, 2-(2-aminoethoxy)ethylamine, are recycled into the reaction of DEG with ammonia.

In order to avoid accumulations of individual components in the circuit of the production installation, a substream of the distillate removed in the column top is preferably discharged. The proportion of the recycled stream is preferably 40%-100% by weight, particularly preferably 50%-100% by weight, of the distillate removed in the column top.

The ADG-comprising stream which is removed in the side draw at column K60 is preferably supplied to a column K70 in which ADG is removed via a side draw, organic products having a boiling point ≥224.8° C. (1.013 bar), in particular >235° C. (1.013 bar) are removed via the bottom and organic products having a boiling point ≤224.8° C. (1.013 bar) are removed overhead.

Column K70 preferably has in the range from 10 to 80, in particular in the range from 20 to 70, theoretical plates.

It is preferably operated at a pressure in the range from 0.005 to 1 bar, in particular 0.01 to 0.7 bar.

The feed point for column K70 is preferably located in the upper or middle, preferably middle, third, based on the number of theoretical plates.

The ADG side draw lying opposite is preferably located 1 to 30, in particular 2 to 25, theoretical plates above the feed point.

Products removed via the bottom in column K70, such as for example DEG, morpholylaminodiglycol, morpholinodiglycol, are preferably recycled into the reaction of DEG with ammonia. (Morpholylaminodiglycol=4-(2-(2-aminoethoxy)ethyl)morpholine, $C_8H_{18}N_2O_2$; morpholinodiglycol (morpholinylethoxyethanol) CAS No. 3603-45-0, $C_8H_{17}NO_3$)

Products removed overhead in column K70, such as for example ADG, N-(2-aminoethyl)morpholine, 2-(2-aminoethoxy)ethylamine, are preferably recycled into the reaction of DEG with ammonia.

The proportion of the recycled stream is preferably 80%-100% by weight, particularly preferably 95%-100% by weight, of the distillate removed in the column top.

In a further particularly preferred embodiment, column K60 is a dividing wall column (DWC).

The dividing wall column (DWC) preferably has a dividing wall (DW) in the longitudinal direction of the column, forming an upper shared column region (1), a lower shared column region (6), an inflow section (2, 4) having a rectifying section (2) and a stripping section (4), and an offtake section (3, 5) having a rectifying section (3) and a stripping section (5), where the bottoms output from K30 is supplied in the upper or middle third, in particular upper third, of the inflow section (2, 4), based on the number of theoretical plates in the inflow section, organic products having a boiling point >255° C. (1.013 bar) are removed via the bottom, organic products having a boiling point ≤224.8° C. (1.013 bar) are removed overhead, ADG is removed from column region 1 and, optionally, preferably in a particular embodiment, vaporous organic products having a boiling point ≥224.8° C. (1.013 bar), in particular >235° C. (1.013 bar), such as for example DEG, are removed from the upper or middle third, in particular upper third, of the offtake section (3, 5) (side draw) based on the number of theoretical plates in the offtake section.

Organic products removed in column K60 via the vaporous side draw, such as for example DEG, are preferably recycled into the reaction of DEG with ammonia.

In a further advantageous embodiment, the dividing wall column (DWC) has a dividing wall (DW) in the longitudinal direction of the column, forming an upper shared column region (1) and (2), an inflow section (3, 4) having a rectifying section (3) and a stripping section (4), and a section (5), wherein the dividing wall DW extends down to the bottom of the column, where the bottoms output from K30 is supplied in the upper or middle third, in particular upper third, of the inflow section (3, 4), based on the number of theoretical plates in the inflow section, DEG and organic products having a boiling point ≥224.8° C. (1.013 bar), preferably >235° C. (1.013 bar), are removed via the bottom below section 5, organic products having a boiling point >255° C. (1.013 bar) (high boilers=HB) are removed via the bottom below sections 3 and 4, organic products having a boiling point ≤224.8° C. (1.013 bar) are removed overhead and ADG is removed from the middle section of the upper shared column region (1) and (2) (side draw).

The dividing wall column K60 preferably has in the range from 30 to 100, in particular in the range from 40 to 90, theoretical plates.

It is preferably operated at a pressure in the range from 0.005 to 1 bar, in particular 0.01 to 0.7 bar.

The subsection of the column DWC, which is divided by the dividing wall (DW) and consists of the subsections 3, 4 and 5 or 2, 3, 4 and 5, or parts thereof in each case, is preferably equipped with structured packings, random packings and/or trays. The dividing wall in these subsections is preferably designed to be thermally insulating.

In a preferred embodiment, the organic products removed overhead in column K60, such as for example N-(2-aminoethyl)morpholine, 2-(2-aminoethoxy)ethylamine, are not discharged but instead are recycled into the reaction of DEG with ammonia.

Products removed via the bottom in column K60, with a dividing wall DW extending down to the bottom of the column, below section 5 removed organic products, such as for example DEG, are preferably recycled into the reaction of DEG with ammonia.

The proportion of the recycled stream is preferably 80%-100% by weight, particularly preferably 95%-100% by weight, of the distillate removed in the column top.

The process according to the invention is advantageous in particular embodiments when using a dividing wall column (DWC) because of a low heat requirement with respect to the 2- or 3-column arrangement (K60-K70 or K80) and also because of the reduction in the number of columns.

In a particular embodiment of the process according to the invention, the ADG-comprising stream(s) which is/are removed overhead at columns K60 and/or K70 is/are supplied wholly or partially to a column K80 in which ADG and organic products having a boiling point ≥224.8° C. (1.013 bar) are removed via the bottom and organic products having a boiling point ≤224.8° C. (1.013 bar) are removed overhead.

The ADG obtained in the bottom can be utilized as a product of value.

ADG in particularly pure form is preferably additionally removed in column K80 via a side draw. In this case, products removed via the bottom in column K80 are preferably recycled into the feed of columns K60 and/or K70.

Products removed overhead in column K80 are preferably recycled into the reaction of DEG with ammonia.

In order to avoid accumulations of individual components in the circuit of the production installation, a substream of the distillate removed in the column top is preferably discharged. The proportion of the recycled stream is preferably 0%-100% by weight, particularly preferably 0%-50% by weight, of the distillate removed in the column top.

Column K80 preferably has in the range from 10 to 80, in particular in the range from 15 to 60, theoretical plates.

It is preferably operated at a pressure in the range from 0.005 to 3 bar, in particular 0.01 to 2 bar.

The feed point for column K80 is preferably located in the upper or middle, preferably upper, third, based on the number of theoretical plates.

The ADG side draw lying opposite is preferably located 1 to 30, in particular 2 to 25, theoretical plates below the feed point.

In a preferred embodiment, the stream comprising organic products which is removed via the bottom at column K60 is supplied to an evaporator V2 in which morpholine aminodiglycol, morpholine diglycol and DEG are removed in gaseous form. These may be used, for example, for the preparation of dimorpholine diethyl ether (DMDEE). The evaporator V1 is preferably operated at a pressure of from 2 to 25 mbar. The evaporators V2 used may in each case be natural circulation evaporators, forced circulation evaporators, forced circulation flash evaporators, falling-film evaporators, Robert evaporators, kettle-type evaporators, thin-film evaporators or climbing film evaporators. Preference is given to in each case using natural circulation evaporators, forced circulation evaporators, forced circulation flash evaporators, falling-film evaporators, Robert evaporators or kettle-type evaporators. A thin-film evaporator is particularly preferred.

Columns K10 to K80 are typically equipped with an evaporator for heating the bottoms. The evaporators used may in each case be natural circulation evaporators, forced circulation evaporators, forced circulation flash evaporators, falling-film evaporators, Robert evaporators, kettle-type evaporators, thin-film evaporators or climbing film evaporators. Preference is given to in each case using natural circulation evaporators, forced circulation evaporators, forced circulation flash evaporators, falling-film evaporators, Robert evaporators or kettle-type evaporators.

For heating the bottoms, the distillation columns K10, K20, K30, K50, K60 and K70 are preferably equipped with an evaporator into which is fed heating vapor having a pressure of from 2 to 50 bar, preferably 3 to 45 bar and particularly preferably 4 to 40 bar.

The process according to the invention is additionally advantageous in particular embodiments because of the following thermal integration measures:

The heat from the vapors from K80 can be integrated in K50.

The heat from the vapors from K70 can be integrated in K50 and/or K80, preferably in K50.

The heat from the vapors from K60 can be integrated in K50.

The heat from the vapors from K40 can be integrated in K20, and/or K80.

The heat from the vapors from the dividing wall column K60 can be integrated in K50.

This thermal integration can be implemented as follows:

In order to be able to utilize the vapor heat generated to a maximum extent, it is preferable to dispense with a heat transfer medium and for the vapor streams to preferably be condensed directly in the corresponding evaporators, instead of the heating vapor. Preference is given to the evaporators mentioned above. The residual vapors are preferably in each case liquefied in a recondenser.

It is additionally advantageous to remove the heat of reaction from the synthesis of the mixture to be separated, in particular via evaporative cooling (water vapor), and to integrate it in the distillation. For the synthesis, embodiments (A) and (B) are preferred in particular, in particular embodiment (A).

The heat of reaction can in this case be integrated in the columns K20, K50, K30, K40, K70 and/or K80, preferably in the columns K20, K40 and/or K80.

In a further preferred embodiment relating to thermal integration, heating vapor for the column K40 is obtained by means of flash evaporation of a condensate resulting from the condensation of heating vapor in a heat exchanger, wherein the heating vapor prior to its condensation in the heat exchanger has a pressure of from 2 to 50 bar, preferably 3 to 45 bar, particularly preferably 4 to 40 bar. In this case, the pressure of the heating vapor which is fed into the heat exchanger is necessarily greater than the pressure of the heating vapor which is obtained by means of flash evaporation and is fed into the evaporator of K40. This type of thermal integration is enabled by the fact that the column is operated at the low pressure according to the invention. According to the invention, the heating vapor for column K40 can be obtained wholly or partially by means of flash evaporation of a corresponding condensate. It is possible for a portion of the remaining heat required to be provided by water vapor from the grid (pressure range: 1 to 10 bar). Typically, at least 50%, preferably at least 60%, particularly preferably at least 70% and very particularly preferably at least 80% or even at least 90% of the heating vapor required is obtained by means of flash evaporation. It is also possible for the heating vapor to be obtained wholly by means of flash evaporation.

The flash evaporation is typically implemented technically in such a way that the vapor condensed in the heat exchanger is (partially) expanded in a suitable vessel. The condensate evaporates as a result and is once again available as heating vapor. The heating vapor thus obtained necessarily has a lower pressure than that which was originally fed into the heat exchanger.

A possible heat exchanger is in principle any heat exchanger which is operated with heating vapor having an appropriate pressure. It does not, therefore, have to be a heat exchanger belonging to the process according to the invention. It is preferably the heat exchanger W2 (see below) or the evaporator of one of the columns K10, K20, K30, K50, K60 or K70. The invention is in addition not restricted such that the thermal integration is effected with precisely one heat exchanger (for example K10). Depending on the amount of heat required in K40, it is also possible for the thermal integration in K40 to be effected from two or more heat exchangers (for example K10 and K20). It is likewise possible for remaining heat still required to be provided by water vapor from the grid as described above.

In a preferred embodiment, the reaction mixture from the reaction of DEG with ammonia, prior to being supplied to column K10, is supplied to an evaporator V1 in which a portion of the ammonia, preferably 20% to 80% by weight of the ammonia present in the feed stream, is removed in gaseous form. The evaporator V1 is preferably operated at a pressure of from 14 to 25 bar. The same evaporators may be used as those mentioned above for V2. Very particularly preferably, V2 is a kettle-type evaporator.

Heating vapor having a pressure of from 1 to 10 bar, preferably 1 to 8 bar, particularly preferably 1 to 6 bar or even 2 to 5 or 2 to 3 bar, is preferably fed into the evaporator V1.

In a particularly preferred embodiment, heating vapor for the evaporator V1 is obtained by means of flash evaporation of a condensate resulting from the condensation of heating vapor in a heat exchanger, wherein the heating vapor prior to its condensation in the heat exchanger has a pressure of from 2 to 50 bar, 3 to 45 bar, particularly preferably 4 to 40 bar. In this case, the pressure of the heating vapor which is fed into the heat exchanger is necessarily greater than the pressure of the heating vapor which is obtained by means of flash evaporation and is fed into the evaporator V1. According to the invention, the heating vapor for the evaporator V1 can be obtained wholly or partially by means of flash evaporation of a corresponding condensate. It is possible for a portion of the remaining heat required to be provided by water vapor from the grid (pressure range: 1 to 10 bar). Typically, at least 50%, preferably at least 60%, particularly preferably at least 70% and very particularly preferably at least 80% or even at least 90% of the heating vapor required is obtained by means of flash evaporation. It is also possible for the heating vapor to be obtained wholly by means of flash evaporation.

A possible heat exchanger is in principle any heat exchanger which is operated with heating vapor having an appropriate pressure. It does not, therefore, have to be a heat exchanger belonging to the process according to the invention. The heat exchanger is preferably the heat exchanger W2 or the evaporator of one of the columns K10, K20, K30, K50, K60 or K70. The invention is in addition not restricted such that the thermal integration is effected with precisely one heat exchanger (for example K10). Depending on the amount of heat required in V1, it is also possible for the thermal integration in V1 to be effected from two or more heat exchangers (for example K10 and K20). It is likewise possible for remaining heat still required to be provided by water vapor from the grid as described above.

Otherwise, the statements made above with respect to the thermal integration in K40 apply correspondingly.

In those embodiments in which thermal integration is effected both in K40 and in the evaporator V1, the heating vapor obtained by means of flash evaporation can originate either from the same or from different heat exchangers. For example, thermal integration in K40 and V1 may be effected exclusively from the evaporator of K10. It is also possible for the thermal integration in K40 to be effected from the evaporator of K10 and for the thermal integration in V1 to be effected from the evaporator of K20.

The process according to the invention is advantageous in particular for the preparation of morpholine (MO) having a purity of 99.5% by weight, in particular 99.6% by weight, for example 99.65% to 99.95% by weight, a content of N-ethylmorpholine (EMO) of 0.20% by weight, in particular 0.10% by weight, for example 0.01% to 0.08% by weight, a content of 1,2-ethylenediamine (EDA) of 0.30% by weight, in particular 0.20% by weight, for example 0.05% to 0.15% by weight, a content of 2-methoxyethanol (MOE) of <0.3% by weight, in particular 0.10% by weight, especially 0.04% by weight to 0.1% by weight, and a content of water of 0.05% by weight, in particular 0.04% by weight, for example 0.01% to 0.03% by weight.

It is advantageous very particularly for the preparation of morpholine (MO) having an APHA color number of ≤10, in particular ≤8, for example 2 to 7, and a chloride content of ≤15 mg/liter, in particular ≤5 mg/liter, very particularly ≤1 mg/liter, for example 0.1 to 0.9 mg/liter.

The process according to the invention is advantageous more particularly for the preparation of monoaminodiglycol (ADG) having a purity of ≥98.00% by weight, in particular ≥98.30% by weight, for example 98.50% to 99.50% by weight, a content of DEG of 0.40% by weight, in particular 0.10% by weight, for example 0.01% to 0.08% by weight, a content of water of 0.20% by weight, in particular 0.10% by weight, for example 0.01% to 0.08% by weight, and an APHA color number of 20, in particular 15, very particularly 10, for example 2 to 8.

The process according to the invention is advantageous more particularly for the preparation of N-ethylmorpholine (EMO) having a purity of ≥98.50% by weight, in particular ≥99.00% by weight, for example 99.50% to 99.90% by weight, a content of water of ≤0.30% by weight, in particular ≤0.20% by weight, for example 0.05% to 0.15% by weight, and an APHA color number of 50, in particular 20, very particularly 10, for example 2 to 8.

APHA color numbers are determined in accordance with DIN EN 1557.

The water content is determined in accordance with DIN 51777 (K. Fischer).

The chloride content is determined by means of ion chromatography (detection of conductivity with chemical suppression) according to the following method:

Sample preparation: Approx. 2 g of sample are weighed into a measuring flask (10 ml) and made up to the mark with eluent.

Measurement Conditions

Ion chromatography system: Metrohm modular system (733)

Precolumn: e.g. DIONEX AG 12; separating column: e.g. DIONEX AS 12

Eluent: e.g. 2.7 mmol of $Na_2CO_3$, 0.28 mmol/l of $NaHCO_3$ in water

Flow rate: 1 ml/min; metered volume: 100 µl

Detection: conductivity after chemical suppression

Suppressor: Metrohm module 753

Regenerant: 50 mmol of $H_2SO_4$ in ultrapure water, (flow rate approx. 0.4 ml/min)

Calibration: external, checked by standard addition experiments

Determination limit: 0.1 mg/kg of chloride in the sample.

The content of morpholine, 1,2-ethylenediamine, N-ethylmorpholine and 2-methoxyethanol in the product of value morpholine is determined by means of GC (GC conditions: 30 m DB-1; temperature program with 60° C. starting temperature, 4° C./min heating rate, 190° C. final temperature).

The content of ADG and DEG in the product of value ADG is determined by means of GC (GC conditions: 30 m DB1; temperature program with 100° C. starting temperature, 8° C./min heating rate, 250° C. final temperature).

A particularly preferred embodiment of the process (see FIG. 5) is illustrated hereinbelow.

Diglycol (DEG) is mixed with the bottoms product from column K70 (main components diglycol and morpholyl-ADG) and the top products from the columns K60 and K70 (main components: aminodiglycol, (2-aminoethyl)morpholine and 2-(2-aminoethoxy)ethylamine) and supplied continuously to the heat exchanger W1.

Liquid ammonia is mixed with recycled ammonia from column K10 and supplied continuously to the heat exchanger W1. Both streams are mixed upstream of the heat exchanger W1 with the cycle gas consisting predominantly of hydrogen. The cycle gas is brought up by means of the compressor D1 from the high-pressure separator B1 placed at the outlet from the synthesis. From the heat exchanger W1, the mixture is heated by a heater W2 and conveyed to the reactor C1. The diglycol is converted over the fixed bed catalyst there into aminodiglycol and morpholine. The reactor output is then cooled down in the heat exchangers W1, W3 and the air cooler W4. Separation into a gas phase and liquid phase is effected in the high-pressure separator B1. The gas phase is—as described above—led as cycle gas to the heat exchanger W1.

The liquid phase is expanded from the high-pressure separator B1 into the medium-pressure separator B2. The so-called suspended gas which is released there is passed into an absorber for recovery of $NH_3$. The amount of hydrogen to be supplemented is taken from the grid and fed in at the synthesis feed.

From the medium-pressure separator B2, the reaction mixture then passes via the heat exchanger W3 into the evaporator V1.

Ammonia Removal (V1 and K10)

In V1, a portion of the ammonia is removed from the reaction mixture. The remaining ammonia is distilled off in column K10 and recycled to the reactor inlet. In addition, a portion of the top product from K20 is supplied to column K10. The heating vapor condensed in the evaporator of K10 is evaporated once more by means of flash evaporation and subsequently supplied to the evaporator V1.

Water Removal (K20)

Water of reaction is removed in column K20. The distillate, which predominantly comprises water and a few low boilers (predominantly ethylmorpholine), is led to column K50. In addition the top product from the morpholine purifying distillation K40 (main components: 1,2-ethylenediamine, morpholine and water) and a portion of the top product from K30 are supplied to column K20. The largely anhydrous bottoms from K20 (main components: morpholine, aminodiglycol, diglycol and high-boiling residue) are supplied to column K30. The heating vapor condensed in the evaporator of K20 is evaporated once more by means of flash evaporation and subsequently supplied to the evaporator of column K40.

LB/HB Removal (K30)

In column K30, the bottom draw from column K20 is separated into a low boiler fraction (main component: morpholine) and a high boiler fraction (main components: aminodiglycol, diglycol and high-boiling residue). The bottoms are supplied to column K60. The condensate is supplied to column K40.

Morpholine Purifying Distillation (K40)

In column K40, morpholine is removed in a gaseous side draw. The top distillate (main components: 1,2-ethylenediamine, morpholine and water) is recycled to K20 or discharged batchwise via a vessel after accumulation of ethylenediamine. The bottoms from column K40 (morpholine and methoxyethanol with higher-boiling secondary components) are combusted. The evaporator of K40 is operated with heating vapor obtained by means of flash evaporation of the heating vapor condensed in the evaporator of K10.

Ethylmorpholine Distillation (K50)

In column K50, N-ethylmorpholine is removed from the feed as an azeotrope with water. The bottoms from the column are discharged.

Residue Removal (K60)

In column K60, aminodiglycol and diglycol are removed from the feed together as a liquid side draw and conveyed to column K70. The distillate from the column (main components: aminoethoxyethylamine, aminoethylmorpholine, aminodiglycol) is returned to the reactor inlet. The bottoms from the column are supplied to the evaporator (V2), where morpholine aminodiglycol (MADG), morpholine diglycol (MDG) and diethylene glycol (DEG) are removed.

Aminodiglycol Distillation (K70)

In column K70, aminodiglycol is removed from the feed at the side draw. The condensate from the column (main components: aminodiglycol, (2-aminoethyl)morpholine and 2-(2-aminoethoxy)ethylamine) is recycled to the reactor inlet. The bottoms from the column are likewise recycled to the reactor inlet.

In the figures:

FIG. 1 shows, inter alia, the obtaining, according to the invention, of MO and ADG by means of a 7-column arrangement. In addition, the thermal integration of the heating vapor (HV) from the evaporator of K10 by means of flash evaporation into the evaporator of K40 is illustrated by way of example. Additionally illustrated are the partial recycling of the top product from K20 into the feed of column K10 and also the partial recycling of the top product from K30 into the feed of column K20.

Figure 2:
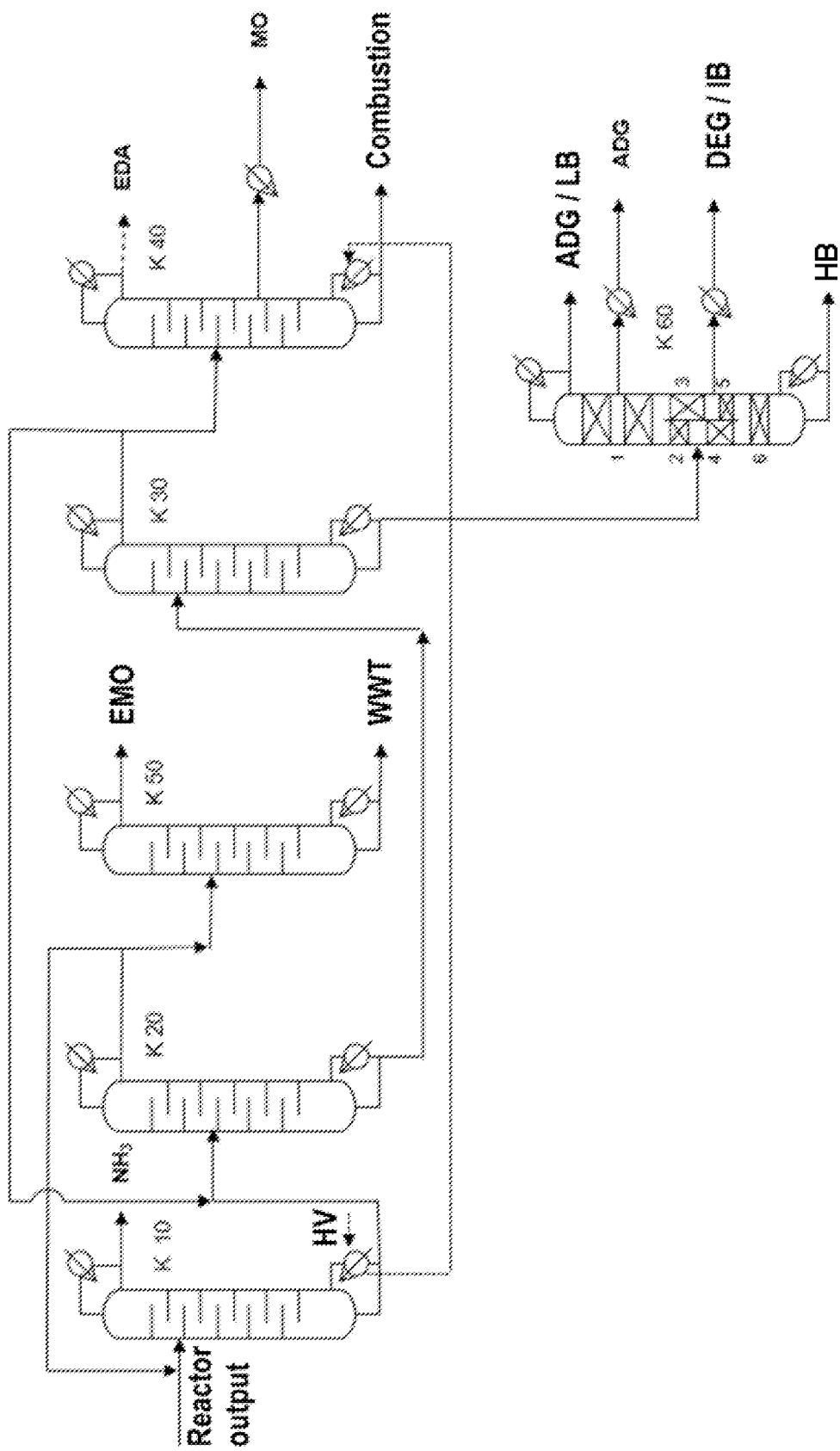

FIG. 2 shows, inter alia, the replacement of columns K60-K70 of the 7-column arrangement with a dividing wall column (DWC). In addition, the thermal integration of the heating vapor (HV) from the evaporator of K10 by means of flash evaporation into the evaporator of K40 is illustrated by way of example. Additionally illustrated are the partial recycling of the top product from K20 into the feed of column K10 and also the partial recycling of the top product from K30 into the feed of column K20.

Figure 3:
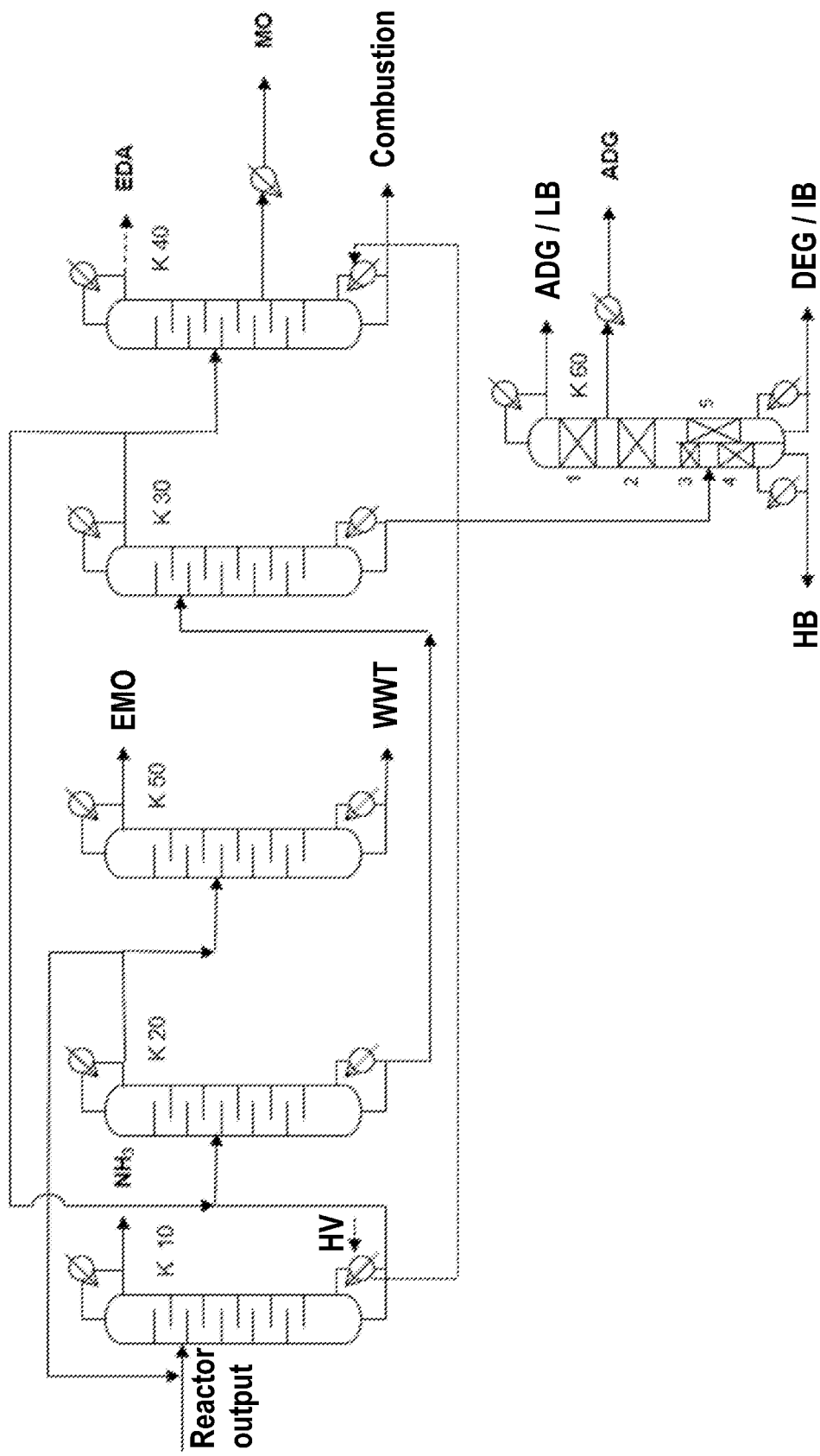

FIG. 3 shows, inter alia, a particular embodiment of the dividing wall column K60 in which the dividing wall (DW) extends down to the bottom of the column. In addition, the thermal integration of the heating vapor (HV) from the evaporator of K10 by means of flash evaporation into the evaporator of K40 is illustrated by way of example. Additionally illustrated are the partial recycling of the top product from K20 into the feed of column K10 and also the partial recycling of the top product from K30 into the feed of column K20.

Figure 4:
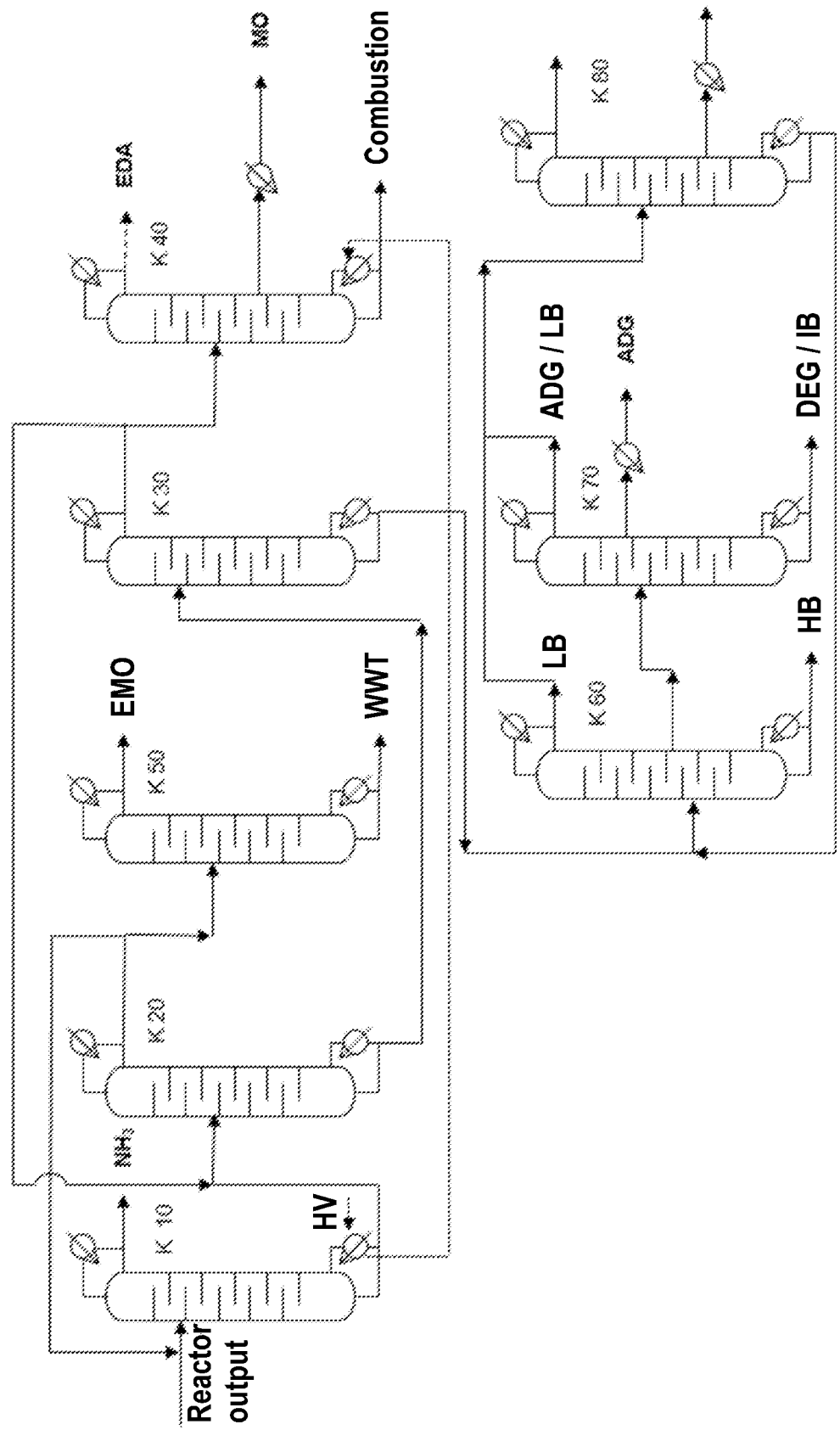

FIG. 4 shows, inter alia, the obtaining, according to the invention, of MO and ADG by means of an 8-column arrangement. In addition, the thermal integration of the heating vapor (HV) from the evaporator of K10 by means of flash evaporation into the evaporator of K40 is illustrated by way of example. Additionally illustrated are the partial recycling of the top product from K20 into the feed of column K10 and also the partial recycling of the top product from K30 into the feed of column K20.

Figure 5:
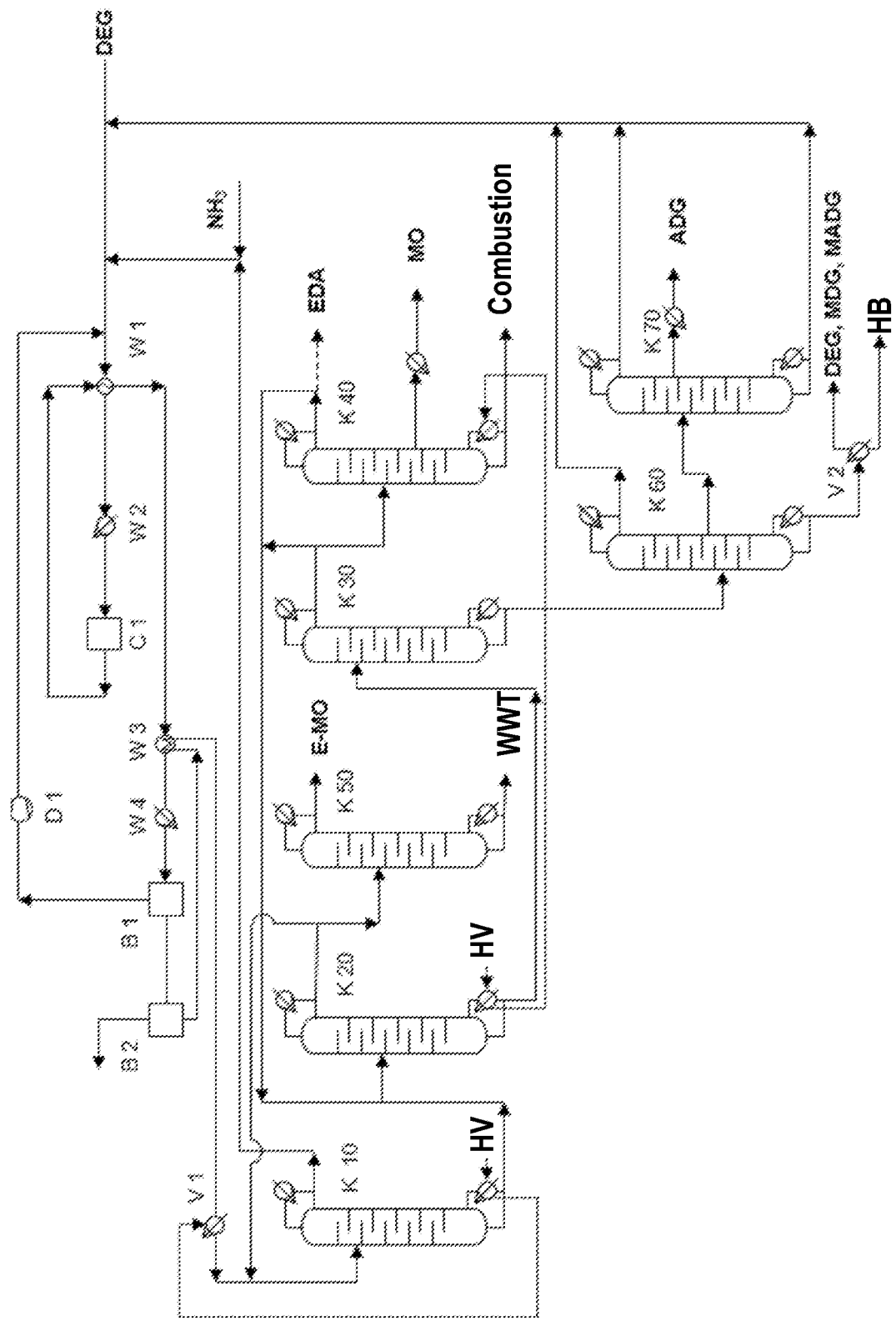

FIG. 5 shows the particularly preferred embodiment of the process according to the invention illustrated above.

HV=heating vapor, HB=high boilers, LB=low boilers, IB=intermediate boilers, WWT=wastewater requiring treatment.

The thermal integration by means of flash evaporation is illustrated in FIGS. 1 to 5 by means of a dashed line.

EXAMPLES

The following examples are based on simulation results obtained with the Aspen Plus software from Aspen Technology, Inc. The thermodynamic parameters used in the program for the individual reaction products are based on published thermodynamic data or in-house measurements. The specification and the simulation of the specified distillation columns used were effected with the customary routines included in the software.

To optimize the simulation model, the simulated results were compared with experimental results, where available, and the simulation model was aligned with the experimental results so that a good agreement between simulation and experimental data was able to be achieved.

The following examples were computed using the optimized simulation model.

Unless indicated otherwise, all figures for pressure in the examples listed here relate to absolute pressure.

Example 1

Purifying Distillation of Morpholine

|  |  | 2.2 bar | 500 mbar | 200 mbar |
|---|---|---|---|---|
| Feed | kg/h | 1973 | 1767 | 1767 |
| Reflux | kg/h | 2484 | 7795 | 5650 |
| Draw (distillate) | kg/h | 120 | 120 | 120 |
| Side draw | kg/h | 1643 | 1630 | 1630 |
| Draw (bottoms) | kg/h | 210 | 17 | 17 |
| Bottom temperature | ° C. | 160.5 | 119 | 100 |
| Evaporator | kW | 845 | 1588 | 1085 |
| Composition of purified morpholine | | | | |
| Morpholine | % by weight | 99.61 | 99.76 | 99.75 |
| 1,2-EDA | % by weight | 0.18 | 0.18 | 0.18 |
| Methoxyethanol | % by weight | 0.13 | 0.03 | 0.03 |
| EMO | % by weight | 0.07 | 0.02 | 0.03 |
| Water | % by weight | — | — | |
| AEOEA | % by weight | 0.01 | 0.01 | 0.01 |
| Total % by weight | | 100 | 100 | 100 |
| Composition of K40 feed | | | | |
| Morpholine | % by weight | 93.93 | 95.3 | 98.04 |
| 1,2-EDA | % by weight | 5.6 | 4.14 | 1.33 |
| Methoxyethanol | % by weight | 0.12 | 0.12 | 0.12 |
| EMO | % by weight | 0.08 | 0.07 | 0.07 |
| Water | % by weight | 0.06 | 0.07 | 0.07 |
| AEOEA | % by weight | 0.21 | 0.3 | 0.37 |
| Total % by weight | | 100 | 100 | 100 |
| Composition of K40 bottoms | | | | |
| Morpholine | % by weight | 97.8 | 53.8 | 47.2 |
| Methoxyethanol | % by weight | 0.15 | 9.5 | 9.6 |
| EMO | % by weight | 0.2 | 4.8 | 3.9 |
| AEOEA | % by weight | 1.85 | 31.9 | 39.3 |
| Total % by weight | | 100 | 100 | 100 |
| Composition of K40 distillate | | | | |
| Morpholine | % by weight | 9 | 40.2 | 81.9 |
| 1,2-EDA | % by weight | 90 | 58.8 | 17.1 |
| Water | % by weight | 1 | 1 | 1 |
| Total % by weight | | 100 | 100 | 100 |

Abbreviations:
1,2-EDA: 1,2-ethylenediamine
EMO: N-ethylmorpholine
AEOEA: aminoethoxyethylamine

Discussion of the Results

The table above presents the results of the purifying distillation of morpholine at a pressure of 2.2 bar, 500 mbar and 200 mbar. In the pressure range according to the invention (200 and 500 mbar), a markedly improved removability of methoxyethanol is possible. For instance, the content of methoxyethanol in the purified morpholine is merely 0.03% by weight, whereas it is much higher in the case of the pressure not in accordance with the invention (2.2 bar), specifically up to 0.13% by weight.

By operating in the pressure range according to the invention, the energy requirement in the evaporator rises from 845 kW at 2.2 bar to 1588 kW and 1085 kW at 500 and 200 mbar, respectively. At the same time, due to the reduced bottom temperature it is possible to operate the evaporator with heating vapor having a lower pressure. For instance, the heating vapor used to heat the bottoms at a top pressure of 2.2 bar typically has a pressure of 16 bar or more. For the lower top pressures according to the invention, heating vapor having a pressure of from 1 to 10 bar is sufficient. Such heating vapor can be produced more energy efficiently, in particular when thermal integration (flash evaporation) is used.

Example 2

K10 and K20 Both With and Without Recycling

The first table shown below presents the simulation results for a recycling of the stream removed overhead at column K20 into K10.

The second table shown below presents the simulation results for a recycling of the stream removed overhead at column K30 and a recycling of the stream obtained at the side draw from K40 (morpholine) into K20.

It can be seen from the results presented that a corresponding recycling can reduce the temperature in the bottom of K10 and/or K20.

For K10 there is a lowering of the bottom temperature from 236.5° C. to 227° C.

For K20 there is a lowering of the bottom temperature from 254° C. to 228° C.

| K10 | | without recycling | with recycling |
|---|---|---|---|
| Top pressure | bar | 15.8 | 15.8 |
| Draw (distillate) | kg/h | 5337 | 5337 |
| Draw (bottoms) | kg/h | 9070 | 9600 |
| Bottom temp. | ° C. | 236.5 | 227 |
| Feed | kg/h | 14 407 | 14 937 |

| | | Composition Feed | Composition Bottoms | Composition Feed | Composition Bottoms |
|---|---|---|---|---|---|
| Ammonia | % by weight | 37.06 | 0.03 | 35.75 | 0.03 |
| Water | % by weight | 7.20 | 11.44 | 10.47 | 16.29 |
| MMO | % by weight | 0.01 | 0.01 | 0.01 | 0.02 |
| Et-MO | % by weight | 0.03 | 0.04 | 0.03 | 0.05 |
| Morpholine | % by weight | 8.68 | 13.78 | 8.37 | 13.03 |
| 1,2-EDA | % by weight | 0.01 | 0.01 | 0.01 | 0.01 |
| Methoxyethanol | % by weight | 0.02 | 0.03 | 0.02 | 0.03 |
| AEOEA | % by weight | 1.76 | 2.80 | 1.70 | 2.65 |
| AEMO | % by weight | 0.13 | 0.21 | 0.13 | 0.20 |
| ADG | % by weight | 15.91 | 25.27 | 15.34 | 23.88 |
| DEG | % by weight | 24.46 | 38.85 | 23.59 | 36.71 |
| IB | % by weight | 4.37 | 6.94 | 4.21 | 6.55 |
| HB | % by weight | 0.37 | 0.59 | 0.36 | 0.56 |
| TOTAL | % by weight | 100 | 100 | 100 | 100 |

| K20 | | without recycling | with recycling |
|---|---|---|---|
| Top pressure | bar | 4.4 | 4.4 |
| Draw (distillate) | kg/h | 1045 | 1575 |
| Draw (bottoms) | kg/h | 8145 | 10 346 |
| Bottom temp. | ° C. | 254 | 228 |
| Feed | kg/h | 9190 | 11 921 |

| | | Composition Feed | Composition Bottoms | Composition Feed | Composition Bottoms |
|---|---|---|---|---|---|
| Ammonia | % by weight | 0.03 | 0.00 | 0.02 | 0.00 |
| Water | % by weight | 11.31 | 0.02 | 13.13 | 0.02 |
| MMO | % by weight | 0.01 | 0.00 | 0.01 | 0.00 |
| Et-MO | % by weight | 0.04 | 0.02 | 0.07 | 0.04 |
| Morpholine | % by weight | 14.63 | 16.49 | 29.40 | 33.85 |
| 1,2-EDA | % by weight | 0.27 | 0.30 | 0.21 | 0.24 |
| Methoxyethanol | % by weight | 0.03 | 0.03 | 0.06 | 0.06 |
| AEOEA | % by weight | 2.77 | 3.12 | 2.40 | 2.76 |
| AEMO | % by weight | 0.21 | 0.24 | 0.18 | 0.20 |
| ADG | % by weight | 24.94 | 28.14 | 19.23 | 22.16 |
| DEG | % by weight | 38.34 | 43.26 | 29.56 | 34.06 |
| IB | % by weight | 6.85 | 7.73 | 5.28 | 6.08 |
| HB | % by weight | 0.58 | 0.66 | 0.45 | 0.52 |
| TOTAL | % by weight | 100 | 100 | 100 | 100 |

Abbreviations Used in Tables 1 and 2

MMO: methylmorpholine
Et-MO: ethylmorpholine
1,2-EDA: 1,2-ethylenediamine
AEOEA: aminoethoxyethylamine
AEMO: aminoethylmorpholine
ADG: aminodiglycol
DEG: diethylene glycol
IB: intermediate boilers
HB: high boilers

The invention claimed is:

1. A process for the continuous distillative separation of mixtures comprising morpholine (MO), monoaminodiglycol (ADG), ammonia, water and methoxyethanol (MOE), obtained by reacting diethylene glycol (DEG) with ammonia, wherein ammonia, water, ADG and DEG are removed by distillation and the resulting stream comprising MO and MOE is supplied to a distillation column K40 in which at a top pressure of from 20 to 2000 mbar MO, MOE and organic products having a boiling point ≥128° C. (1.013 bar) are removed via the bottom and organic products having a boiling point ≥128° C. are removed overhead, and also MO is removed via a side draw, where K40 is equipped with an evaporator for heating the bottoms, into which is fed heating vapor having a pressure of from 1 to 10 bar.

2. The process according to claim 1, wherein, for the distillative removal of ammonia, water, ADG and DEG, a stream comprising ammonia, water, ADG, and DEG is fed to a first distillation column K10, ammonia is removed overhead in a first distillation column K10, the bottoms output from K10 is supplied to a second distillation column K20, in which water and organic products are removed overhead at a top temperature of from 45 to 198° C. and a top pressure of from 0.1 to 15 bar, the bottoms output from K20 is supplied to a third distillation column K30, in which MO, MOE and organic products having a boiling point <140° C. (1.013 bar) (stream comprising MO and MOE) are removed overhead or via a side draw and ADG, DEG and organic products having a boiling point of >190° C. (1.013 bar) are removed via the bottom.

3. The process according to claim 1, wherein the reaction of diethylene glycol (DEG) with ammonia is effected in the presence of hydrogen and a heterogeneous hydrogenation catalyst, wherein
the reaction has a conversion based on DEG of 40% to 75% by weight,
the reaction is effected at a pressure of from 100 to 300 bar and a temperature of from 170° C. to 220° C.,
the molar ratio of ammonia to DEG is 4 to 10, and
a catalyst hourly space velocity in the range from 0.05 to 5 kg of diethylene glycol (DEG) per liter of catalyst (bed volume) and per hour.

4. The process according to claim 2, wherein the stream comprising water and organic products which is removed overhead at column K20 is partially recycled into a feed or bottom of column K10.

5. The process according to claim 2, wherein the water and organic products removed overhead at column K20 are supplied to a distillation column K50 in which aqueous N-ethylmorpholine solution (aqueous EMO solution) is removed overhead or via a liquid side draw and water is removed via the bottom.

6. The process according to claim 2, wherein the ADG, DEG and organic products having a boiling point of >190° C. (1.013 bar) removed via the bottom of K30 are supplied to a distillation column K60 in which an ADG-comprising stream is removed in the side draw, organic products having a boiling point ≤224.8° C. (1.013 bar) are removed overhead and organic products having a boiling point ≥255° C. (1.013 bar) are removed via the bottom.

7. The process according to claim 6, wherein the ADG-comprising stream which is removed in the side draw at K60 is supplied to a distillation column K70 in which ADG is removed via a side draw, organic products having a boiling point ≥224.8° C. (1.013 bar) are removed via the bottom and organic products having a boiling point ≤224.8 (1.013 bar) are removed overhead.

8. The process according to claim 6, wherein column K60 is a dividing wall column (DWC).

9. The process according to claim 6, wherein the ADG-comprising stream which is removed at column K60 is supplied wholly or partially to a column K80 in which ADG and organic products having a boiling point ≥224.8° C. (1.013 bar) are removed via the bottom and organic products having a boiling point ≤224.8 (1.013 bar) are removed overhead.

10. The process according to claim 6, wherein the organic products having a boiling point ≥255° C. (1.013 bar) removed via the bottom at column K60 are supplied to an evaporator V2 in which morpholine aminodiglycol, morpholine diglycol and DEG are removed in gaseous form.

11. The process according to claim 1, wherein the reaction of DEG with ammonia is effected in a reactor C1, wherein DEG and ammonia are heated prior to entry into C1 by means of a heat exchanger W2 into which is fed heating vapor having a pressure of from 2 to 50 bar.

12. The process according to claim 7, wherein columns K10, K20, K30, K60 and K70 are each equipped with an evaporator for heating the bottoms, into which is fed heating vapor having a pressure of from 2 to 50 bar.

13. The process according to claim 1, wherein heating vapor for the column K40 is obtained by means of flash evaporation of a condensate resulting from the condensation of heating vapor in a heat exchanger, wherein the heating vapor prior to its condensation in the heat exchanger has a pressure of from 2 to 50 bar.

14. The process according to claim 2, wherein the reaction of DEG with ammonia is effected in a reactor C1, wherein DEG and ammonia are heated prior to entry into C1 by means of a heat exchanger into which is fed heating vapor having a pressure of from 2 to 50 bar.

15. The process according to claim 14, wherein the heat exchanger is a heat exchanger W2 or an evaporator of the columns K10, K20, or K30.

16. The process according to claim 2, wherein the stream comprising ammonia, water, ADG, and DEG fed to the first distillation column K10, prior to being supplied to column K10, is supplied to an evaporator V1 in which a portion of the ammonia is removed in gaseous form.

17. The process according to claim 16, wherein heating vapor having a pressure of from 1 to 10 bar is fed into the evaporator V1.

18. The process according to claim 17, wherein heating vapor for the evaporator V1 is obtained by means of flash evaporation of a condensate resulting from the condensation of heating vapor in a heat exchanger, wherein the heating vapor prior to its condensation in the heat exchanger has a pressure of from 2 to 50 bar.

19. The process according to claim 7, wherein the reaction of DEG with ammonia is effected in a reactor C1, wherein DEG and ammonia are heated prior to entry into C1 by means of a heat exchanger into which is fed heating vapor having a pressure of from 2 to 50 bar.

20. The process according to claim 19, wherein the heat exchanger is a heat exchanger W2 or an evaporator of one of the columns K10, K20, K30, K60 or K70.

* * * * *